US005951517A

United States Patent [19]
Lampropoulos et al.

[11] Patent Number: 5,951,517
[45] Date of Patent: Sep. 14, 1999

[54] ONE-HAND PULSE PUMP

[75] Inventors: Fred P. Lampropoulos, Sandy; Jerry L. Trujillo, Ogden; M. Mary Sinnott, Park City, all of Utah

[73] Assignee: Merit Medical Systems, Inc., South Jordan, Utah

[21] Appl. No.: 08/950,272

[22] Filed: Oct. 14, 1997

[51] Int. Cl.⁶ ............................................. A61M 1/00
[52] U.S. Cl. ................................................... 604/151
[58] Field of Search ............................. 604/134, 135, 604/151, 152

[56] References Cited

U.S. PATENT DOCUMENTS

| | | | |
|---|---|---|---|
| 1,039,591 | 9/1912 | Prideaux | 604/135 |
| 1,367,008 | 2/1921 | Bessesen . | |
| 1,655,909 | 1/1928 | Laurent . | |
| 2,156,023 | 4/1939 | McKay . | |
| 2,643,655 | 6/1953 | McKay . | |
| 2,845,066 | 7/1958 | Hoppe et al. | 128/218 |
| 3,727,614 | 4/1973 | Kniazuk | 604/152 X |
| 4,020,838 | 5/1977 | Phillips et al. | 128/223 |
| 4,244,366 | 1/1981 | Raines | 128/218 |
| 4,246,932 | 1/1981 | Raines | 137/512 |
| 4,261,359 | 4/1981 | Chein | 128/223 |
| 4,301,795 | 11/1981 | Zimmerman | 604/152 X |
| 4,345,595 | 8/1982 | Whitney et al. | 604/152 X |
| 4,450,079 | 5/1984 | Farr | 604/152 |
| 4,643,723 | 2/1987 | Smit | 604/207 |
| 5,106,370 | 4/1992 | Stewart | 604/135 X |
| 5,267,964 | 12/1993 | Karg | 604/151 X |
| 5,395,312 | 3/1995 | Desai | 604/152 X |

OTHER PUBLICATIONS

Pulse Spray, Pulsed Infusion System, by AngioDynamics, Division of E–Z–EM, Inc., Nov. 1994.

Valji, Karim, Roberts, Anne C., Davis, Gary B., Bookstein, Joseph J., Pulsed–Spray Thrombolysis of Arterial and Bypass Graft Occulsions, *Am J Roentgenology*, vol. 156:617–621, Mar. 1991.

Pulsed Infusion Catheters and Injection Systems, *Industry Attractiveness Model*, Oct. 2, 1996.

Bookstein, Joseph J., Fellmeth, Brian, Roberts, Anne, Valji, Karim, Davis, Gary, Machado, Thomas, Pulsed–Spray Pharmacomechanical Thrombolysis: Preliminary Clinical Results, *American Journal of Roentgenology*, vol. 152:1097–1100, May 1989.

Valji, Karim, Bookstein, Joseph J., Roberts, Anne C., Davis, Gary B., Pharmacomechanical Thrombolysis and Angioplasty in the Management of Clotted Hemodialysis Grafts: Early and Late Clinical Results, *Intervention Radiology*, vol. 178:243–247, 1991.

Hansen, Margaret E., Miller III, George L., Starks, Kenneth C., Pulse–Spray Thrombolysis of Inferior Vena Cava Thrombosis Complicating Filter Placement, *CardioVascular and Interventional Radiology*, vol. 17:38–40, Jan.–Feb. 1994.

Bookstein, Joseph J., Valji, Karim, Pulse–Spray Pharmacomechanical Thrombolysis, *CardioVascular and Interventional Radiology*, vol. 15:228–223, 1992.

Kandarpa, Krishna, Goldhaber, Samuel Z., Meyerovitz, Michael F., Pulse–Spray Thrombolysis: The "Careful Analysis", *Radiology*, vol. 193:320–424, Nov. 1994.

(List continued on next page.)

*Primary Examiner*—Jeffrey A. Smith
*Attorney, Agent, or Firm*—Workman, Nydegger, Seeley

[57] ABSTRACT

A hand operated, fluid dispensing pump includes a body that slidably interacts with a handle. The body includes a valve housing fluid coupled with an inlet passageway, an outlet passageway, and a dispensing barrel. A finger rest rigidly projects from the dispensing barrel. A loading chamber is recessed within the finger rest and is configured to receive a fluid supply syringe. A plunger, mounted to the handle, is slidably received within the dispensing barrel. As the plunger is advanced within the barrel, fluid is dispensed from the pump. Once the plunger is fully advanced, a spring disposed between the body and the handle automatically retracts the plunger within the barrel. As the plunger is retracted within the barrel, the barrel is automatically filled with a fluid from the fluid supply syringe.

34 Claims, 12 Drawing Sheets

OTHER PUBLICATIONS

Robinson, David L., Teitelbaum, George P., Phlegmasia Cerulea Dolens: Treatment by Pulse–Spray and Infusion Thrombolysis, *American Journal of Roetgenology*, vol. 160:1288–1290, Jun. 1993.

Valji, Karim, Bookstein, Joseph J., Roberts, Anne C., Oglevie, Steven B., Pittman, Christopher, O'Neil, Michael P., Pulse–Spray Pharmacomechanical Thrombolysis of Thrombosed Hemodialysis Access Grafts: Long–Term Experience and Comparison of Original and Current Techniques, *American Journal of Roetgenology*, vol. 164:1495–1500, Jun. 1995.

Trerotola, O. Pulse–Spray Thrombolysis of Hemodialysis Grafts: Not the Final Word, *American Journal of Roetgenology*, vol. 164:1501–1503, Jun. 1995.

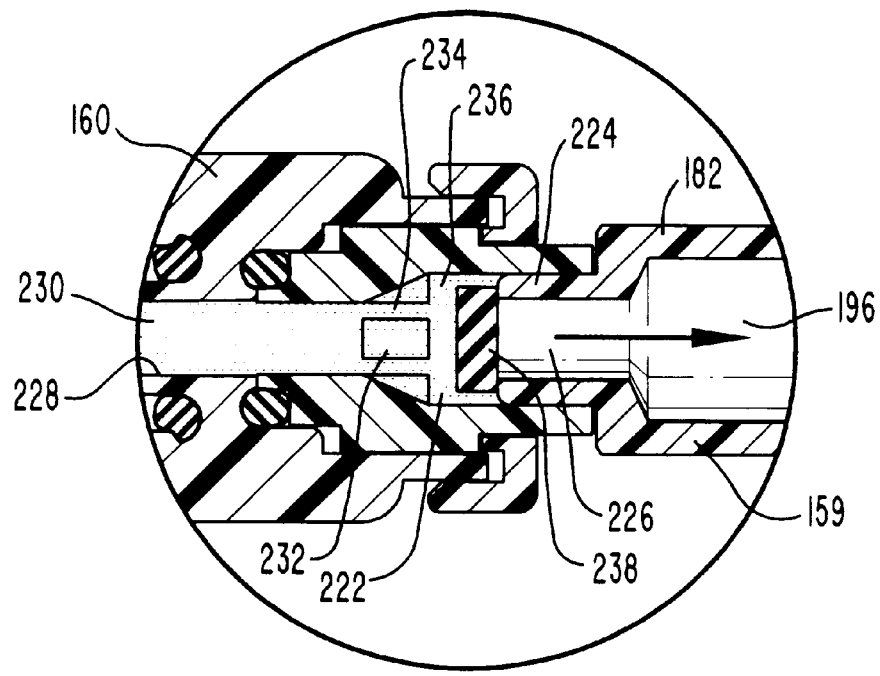
FIG. IIA
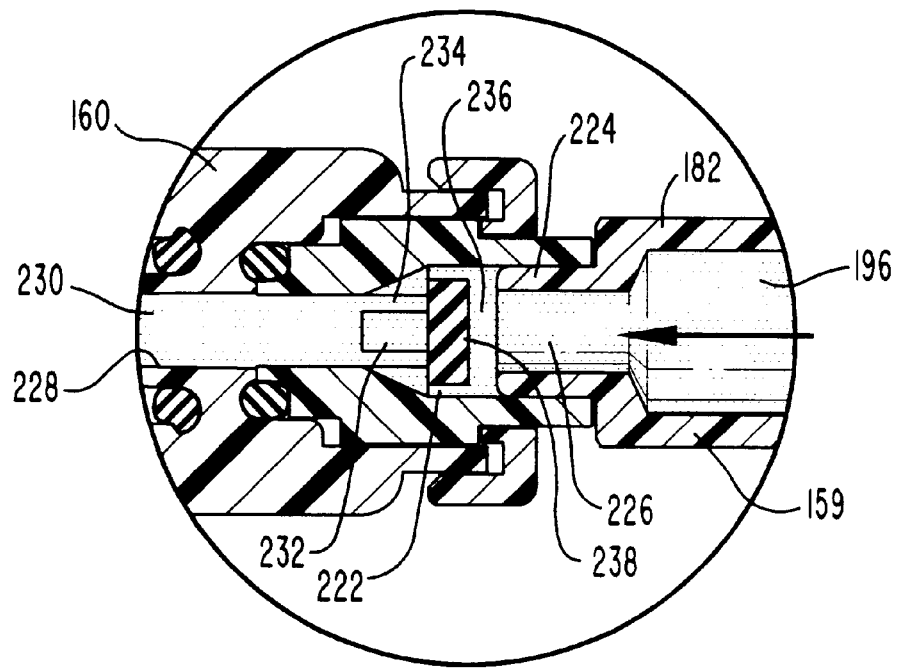
FIG. IIB

ONE-HAND PULSE PUMP

BACKGROUND OF THE INVENTION

1. Field of the Invention

The present invention relates to hand pumps and, more specifically, pumps operated by a single hand for repeatedly dispensing a predetermined amount of a fluid into a catheter.

2. The Relevant Technology

A reasonably common and dangerous medical condition arises when a blood clot develops in the vascular system of the body of a patient. A blood clot or thrombus can endanger the health of a patient in at least two significant ways. First, the clot may restrict or even completely stop essential blood flow to a portion of the patient's body. If the blood flow to the brain or heart for example is restricted the patient's life may be placed in jeopardy. Additionally, a clot may break loose from the site at which it formed and be carried by the blood stream to an organ, such as the heart or lungs, where it may cause irreparable damage or even death. Accordingly, when a blood clot is detected, it must be quickly and effectively treated.

One method involves surgery to remove the clot and repair the blood vessel. A less invasive method uses thrombolytic drugs to break up, or lyse, the thrombus. This method of treating a blood clot consists of inserting a catheter into the patient's vascular system, preferably near the site of the clot. If the catheter enters the vascular system near the clot, the catheter alone may be used. If, for a variety of reasons, the catheter must be inserted into the vascular system at a distance from the clot, placement of the catheter may be aided by using an introducer sheath and a guide wire, which can be used to push and guide the catheter through the veins or arteries of the vascular system to reach the clot.

Once the catheter is positioned at the site of the clot, a thrombolytic fluid capable of dissolving the clot, such as urokinase or streptokinase, is delivered to the site of the clot by means of the catheter. Conventional catheters have a lumen, i.e., an internal passage, that allows the thrombolytic fluid to flow through the catheter to one or more discharge openings at or near the distal end of the catheter. The discharged thrombolytic fluid then dissolves or lyses the clot, thus removing the danger to the patient.

Not all clots are easily or successfully lysed. Some clots form around arterial lesions, which clots may not be easily lysed or broken up by the thrombolytic fluid and which usually require surgical removal. Additionally, some clots may be extremely thick, extending for a relatively long distance through a blood vessel of the circulatory system. Such a thick clot may require considerable amounts of time and heavy irrigation of thrombolytic fluid to dissolve.

Typically, a guidewire is used in conjunction with a catheter to facilitate placement of the catheter. The guidewire can also serve to penetrate the clot in order to form a passage therethrough so that the catheter can be inserted within the interior of the clot. This helps to ensure that the thrombolytic fluid is concentrated or focused at the location of the clot, since excessive thrombolytic fluid in the bloodstream can have adverse effects on the patient.

After the guide wire has been used to create a narrow passage through the clot, particularly a thick clot, the thrombolytic fluid is released through the one or more openings employing a simple catheter required movement of the catheter from one end of the clot to the other while dispensing the thrombolytic fluid in order to adequately distribute the fluid over the entire length of the thrombus.

Subsequent attempts have been made to improve the dissolution of blood clots by forcefully injecting a dissolving agent simultaneously along the length of the blood clot. In one such approach, the catheter has a large tip opening and a plurality of small side opening positioned at the distal end of the catheter. The tip opening is used for placement of the catheter. Initially, a long thin guide wire is slid into the vascular system such that the distal end of the guidewire extends through the blood clot. An introducer sheath can be used to insert the guidewire. Next, the end of the guidewire outside the body of the patient is received within the tip opening of the catheter. The catheter is then slid over the guidewire, while holding the guidewire stationary, until the side openings in the catheter are positioned within the blood clot. Once the catheter is positioned, the guidewire is removed while holding the catheter stationary.

To force the dissolving agent to pass through the side openings in the catheter, it is first necessary to block or occlude the large tip opening. This is accomplished by inserting a thin placement wire having an enlarged occluding ball at the distal end thereof into the end of the catheter outside of the patient. The placement wire is advanced until the occluding ball is sealingly disposed at the tip opening. With the placement wire still inside the catheter, the proximal end of the catheter is fluid coupled with a two syringe pumping system for injecting the dissolving agent into the catheter and out through the side openings thereof.

The syringe system includes a conventional first syringe coupled to one end of a valve housing having a pair of opposing check valves formed therein. The opposing end of the valve housing is coupled to the proximal end of the catheter. A conventional second syringe is filled with the dissolving fluid and is coupled to the side of the valve housing. As the plunger of the first syringe is manually drawn back, fluid is drawn from the second syringe into the first syringe. A first check valve within the valve housing blocks communication with the catheter to prevent body fluid from being sucked into the catheter. Once a sufficient amount of dissolving fluid is drawn into the first syringe, the plunger thereof is pushed forward. Simultaneously, the first check valve is opened and a second check valve, which block access to the second syringe, is closed. As a result, the dissolving fluid is dispensed into the catheter and out through the side openings, thereby forcefully flowing against the blood clot. The process is then continually repeated by again manually pulling back and advancing the plunger of the first syringe until the blood clot is dissolved.

Although useful, there are several shortcomings associated with the above described syringe pumping system. For example, to ensure that the proper amount of dissolving agent is dispensed through the first syringe, the surgeon must carefully measure the amount of dissolving fluid that is drawn into the syringe. This delicate measuring must be performed each time an injection is made, as there is variability from dose to dose. As a result of this required measuring, the rate at which the fluid is dispensed is substantially reduced. If too much dissolving fluid is drawn into the first syringe, the first syringe must be removed from the valve assembly in order to dispense the excess fluid. In this case, the excess fluid, which is very expensive, is lost. Furthermore, having to remove and reattach the first syringe increases the likelihood of introducing an air bubble into the system. The introduction of an air bubble into the vascular system can be life threatening. Finally, in the event the user attempts to inject a portion of the fluid, the user will not be able to inject it with the forceful stroke needed to mechanically break up the clot.

An additional problem with the above pumping system is that filling the first syringe typically requires two hands. That is, one hand holds and stabilizes the barrel of the syringe while the other hand pulls back the plunger. The use of two hands is further necessitated by the fact that the first syringe must be filled to an exacting amount as discussed above. The requirement that the surgeon use both hands to operate the first syringe and that the surgeon continually concentrate on the first syringe to insure that the first syringe is not over filled, limits the ability of the surgeon to simultaneously perform other tasks, such as stabilizing the catheter and concentrating on the status of the patient. Also to get higher injection pressures some people use two hands to inject as well as to fill the syringe.

Yet another problem with the above syringe system is that conventional syringes dispense by compressing the plunger with the thumb while holding the barrel with the index and middle finger. Although such a system is fine for singular doses, it is preferred in the present system to repeatedly inject the dissolving fluid at short intervals and under high pressures. By using only two fingers and a thumb to operate the first syringe, only minimal pressure can be produced. Furthermore, the hand quickly tires and cramps by using such small and isolated muscles. Thus, some people end up using two hands.

The configuration of the above syringe system is also less than optimal. For example, the first and second syringes as discussed above are long narrow plastic syringes that project at rights angles to each other with their nozzles closely connected. Each syringe is rigidly connected to the valve assembly. In light of the repeatedly applied force to the first syringe, the positioning of the second syringe relative to the first syringe enhances the risk that the second syringe could be broken off or dislodged from the valve assembly. For example, should the surgeon slip during pumping of the first syringe or make any fast hand movements, the surgeon could unintentionally catch the second syringe and potentially break it off.

Finally, yet another problem with the present system is that as a result of the multiple syringes and check valves, it is difficult to debubble the system. That is, all air must be removed from the system prior to injection of the fluid into the vascular system. In the case where saline cannot be used to prime the system, debubbling of the prior art system can require relatively large amounts of dissolving fluid to be run therethrough to ensure that the air bubbles are removed. Such fluid can be very expensive and wasteful. The use of two check valves also increases the number of moving parts and thus increase the likelihood of mechanical failure.

OBJECTS AND BRIEF SUMMARY OF THE INVENTION

Accordingly, it is an object of the present invention to provide improved fluid dispensing pumps for repeatedly dispensing predetermined amounts of a fluid.

Another object of the present invention is to provide improved fluid dispensing pumps wherein the amount of fluid dispensed is selectively controlled and automatically measured.

Also another object of the present invention is to provide improved fluid dispensing pumps wherein the pump can be operated using a single hand.

Another object of the present invention is to provide improved fluid dispensing pumps wherein the fluid can be injected using an increased number of muscles in the hand so as to increase the pressure, frequency, and rate at which the fluid is dispensed.

Yet another object of the present invention is to provide improved fluid dispensing pumps wherein the fluid source is partially enclosed within the pump to prevent accidental breaking off or loosening thereof.

Finally, another object of the present invention is to provide improved fluid dispensing pumps that are more easily debubbled, have minimal moving parts, and a reduced number of luer fittings or other connections.

To achieve the foregoing objects, and in accordance with the invention as embodied and broadly described herein, a fluid dispensing pump is provided. The pump includes a body with a handle slidably attached thereto. The body includes a valve housing coupled with an outlet passageway, an inlet passageway, and the chamber of a dispensing barrel. The body also includes an elongated finger rest having a loading chamber recessed therein. The loading chamber communicates with the inlet passageway. A fluid source, such as a syringe, is selectively inserted into the loading chamber and coupled with the inlet passageway.

The handle includes a plunger housing and an elongated palm rest. The plunger housing bounds a plunger chamber that communicates with the exterior through a port. The free end of the dispensing barrel is positioned within the plunger chamber through the port. A plunger having a tip end is also positioned within the plunger chamber. The tip end of the plunger is slidably received within the dispensing barrel. A control knob is rotatably mounted on the exterior of the dispensing barrel and prevents the dispensing barrel from sliding out through the port. A spring encircles the plunger and extends between the control knob and the handle.

The palm rest of the handle is configured to receive the palm of a user's hand when the fingers of the user's hand are curled around the finger rest. As the fingers are drawn toward the user's palm, the spring is compressed, and the plunger is advanced within the barrel. Simultaneously, a valve positioned within the valve housing is configured in a first position which allows the fluid within the chamber of the barrel to pass from the chamber to the outlet passageway. When the user's fingers on the finger rest are relaxed, the spring automatically separates the body and the handle of the pump, thereby retracting the plunger within the barrel. Simultaneously, the valve moves to a second position allowing fluid to pass from the inlet passageway to the chamber of the dispensing barrel. By selectively rotating the control knob, the distance at which the plunger is able to travel is controlled, thereby controlling the amount of fluid that can be aspirated and dispensed. Accordingly, by repeatedly squeezing the pump, a predetermined amount of fluid is repeatedly dispensed from the pump.

The inventive pump has several unique advantages over prior art systems. For example, as a result of the spring automatically retracting the plunger within the dispensing barrel, the pump can be operated using a single hand. In addition, by selectively positioning the control knob, the surgeon can also automatically set how much fluid will be dispensed with each squeeze of the pump. The dispensing barrel has graduation marks on its exterior surface to allow for plunger and tip placement at the required dose. The surgeon thus does not have to repeatedly measure the amount of fluid going into the dispensing barrel. Furthermore, since the pump is squeezed between all of the fingers and the palm of the hand, the surgeon is able to apply more pressure to the pump. Likewise, the surgeon can squeeze quicker and over a longer period of time. Also injecting using the "squeezing" motion tends to normalize the rate and pressure of injections thereby decreasing variability between users.

An additional advantage of the inventive pump is that it uses only a single valve as opposed to two check valves. The single valve assembly requires fewer moving parts and makes the system easier to debubble. Furthermore, as a result of the loading chamber within the finger rest, the fluid source can be enclosed within the pump, thereby minimizing the potential for breaking off or dislodging of the fluid source.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 11A is a cross-sectional side view of the second check valve shown in the barrel of the pump as shown in FIG. 8;

FIG. 11B is a cross-sectional side view of the second check valve shown in the barrel of the pump as shown in FIG. 9;

DETAILED DESCRIPTION OF THE PREFERRED EMBODIMENTS

Figure 1:
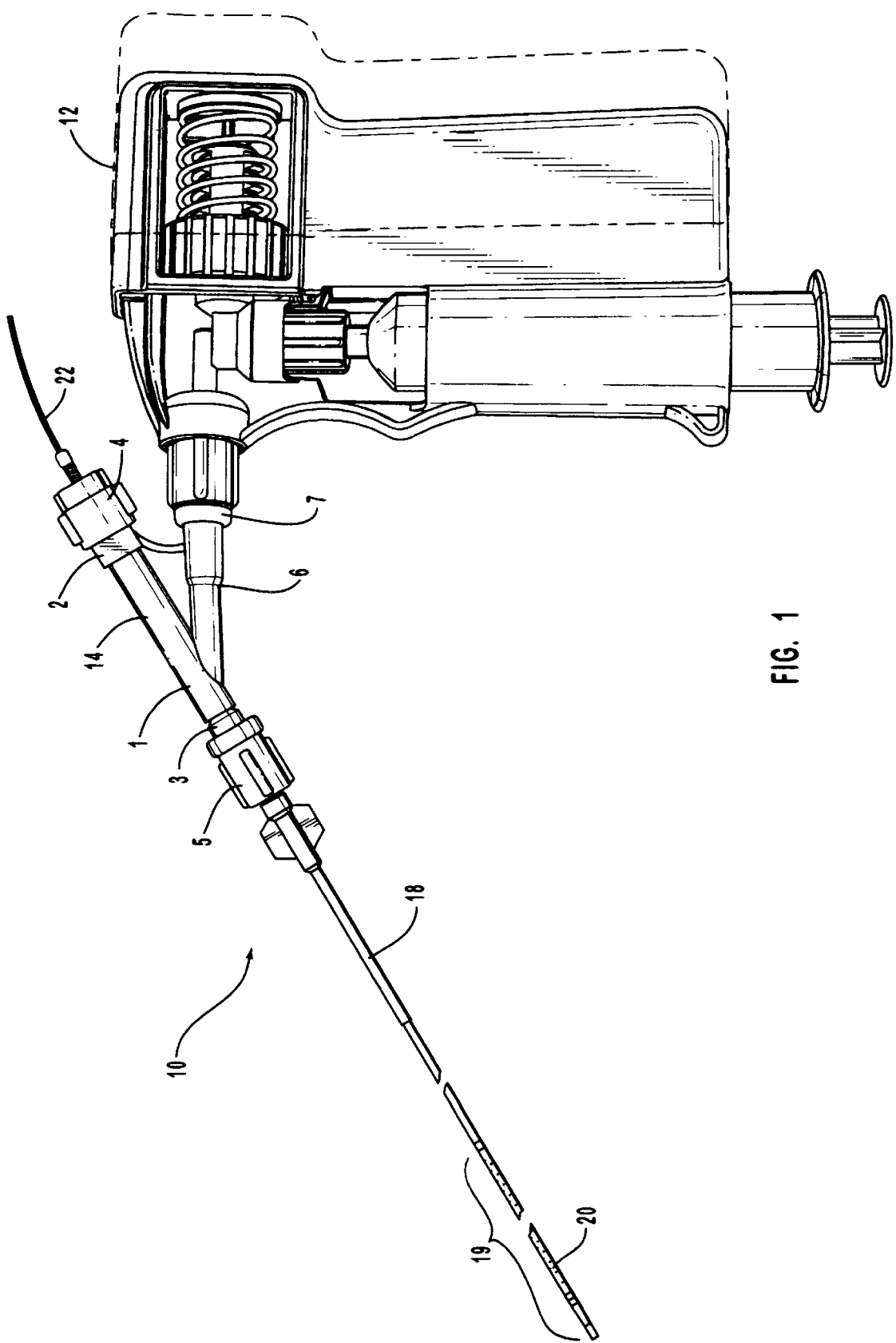
FIG. 1 is a side view of one embodiment of the inventive fluid infusion system.

Depicted in FIG. 1 is one embodiment of a fluid infusion system 10 incorporating features of the present invention.

Infusion system 10 includes a three-way connector 14 having a hollow primary tube 1 extending from a proximal end 2 to a distal end 3. Positioned at proximal end 2 is a knob 4 that is rotatable to selectively close a tubular seal not shown but positioned therein. Positioned at distal end 3 is a conventional rotator connector 5. Three-way connector 14 further includes a hollow secondary tube 6 projecting from primary tube 1 in fluid communication therewith. Secondary tube 6 terminates at a threaded end 7. Three-way connector 14 can include a conventional hemostasis valve. One embodiment of a three-way hemostasis valves is further disclosed in U.S. Pat. No. 5,591,137 entitled "Hemostasis Valve with Locking Seal", and filed Jul. 14, 1995 in the name of Brian Stevens, which patent is incorporated herein by specific reference.

Infusion system 10 further includes a hand operated pump 12 directly fluid coupled to second tube 6 of three-way connector 14. In an alternative embodiment, a flexible tube can be used to fluid couple pump 12 to three-way connector 14. Fluid coupled to distal end 3 of three-way connector 14 is an elongated, pliable infusion catheter 18. Infusion catheter 18 has a distal end 19 with a plurality of infusion holes 20 extending therethrough.

During use, distal end 19 of infusion catheter 18 is selectively positioned within the vascular system of a patient. An occluding wire 22 is inserted into proximal end 2 of three-way connector 14 and then slidably passed through three-way connector 14 and into infusion catheter 18. Occluding wire 22 seals distal end 19 of infusion catheter 18 closed as will be discussed later in greater detail. With occluding wire 22 positioned, knob 4 is rotated on three-way connector 14 so as to seal three-way connector 14 closed around occluding wire 22. A surgeon then manually operates pump 12 so as to repeatedly pump predetermined amounts of a desired fluid into catheter 18. In turn, the fluid is forcefully discharged in small streams out through infusion holes 20 and into the vascular system.

In one use, distal end 19 of infusion catheter 18 can be positioned through or adjacent to a blood clot. The pumped fluid would be a blood clot dissolving agent such as urokinase or streptokinase. It is envisioned however, that infusion system 10 can also be used for other purposes, for example, removing fat or other deposits on the wall of a vein or artery.

The present invention includes pump means fluid coupled to the proximal end of the infusion catheter 18 for repeatedly dispensing predetermined amounts of fluid into the infusion catheter 18. By way of example and not by limitation, depicted in FIG. 2, pump 12 primarily comprises a body 30 that slidably interacts with a handle 32. Body 30 comprises a head 34 positioned at a top end 36 and a hollow finger rest 38 positioned at an opposing bottom end 40. An access opening 42 transversely extends through body 30 between head 34 and finger rest 38. Head 34 includes a valve housing 44 having a nozzle 46 and a dispensing barrel 48 positioned on opposing sides thereof. A rotator connector 47 is attached to nozzle 46. Formed on the exterior of dispensing barrel 48 are engagement threads 50. Projecting from valve housing 44 into access passageway 42 is a stem 52. Stem 52 terminates at a threaded end 54. Head 34 further includes an elongated, inverted T-shaped alignment ridge 56 positioned at top end 36 and extending over dispensing barrel 48.

Finger rest 38 has a substantially cylindrical configuration with an interior surface 57 bounding a cylindrical loading chamber 58. Loading chamber 58 longitudinally extends between access opening 42 and bottom end 40 of body 30. An upper finger grip 60 extends between nozzle 46 and loading barrel 38. A lower finger grip 61 projects from finger rest 38 at bottom end 40 and is in alignment with upper finger grip 60. Projecting from the side of finger rest 38 opposite finger grips 60 and 61 is an elongated coupling plate 62. Extending out from each side of coupling plate 62 are a plurality of spaced apart alignment ridges 64. Coupling plate 62 terminates at an outside edge 63 having a recess 68 formed thereon. A spring post 66 projects out from a recess 68 and is configured to receive a spring 67.

Figure 3:
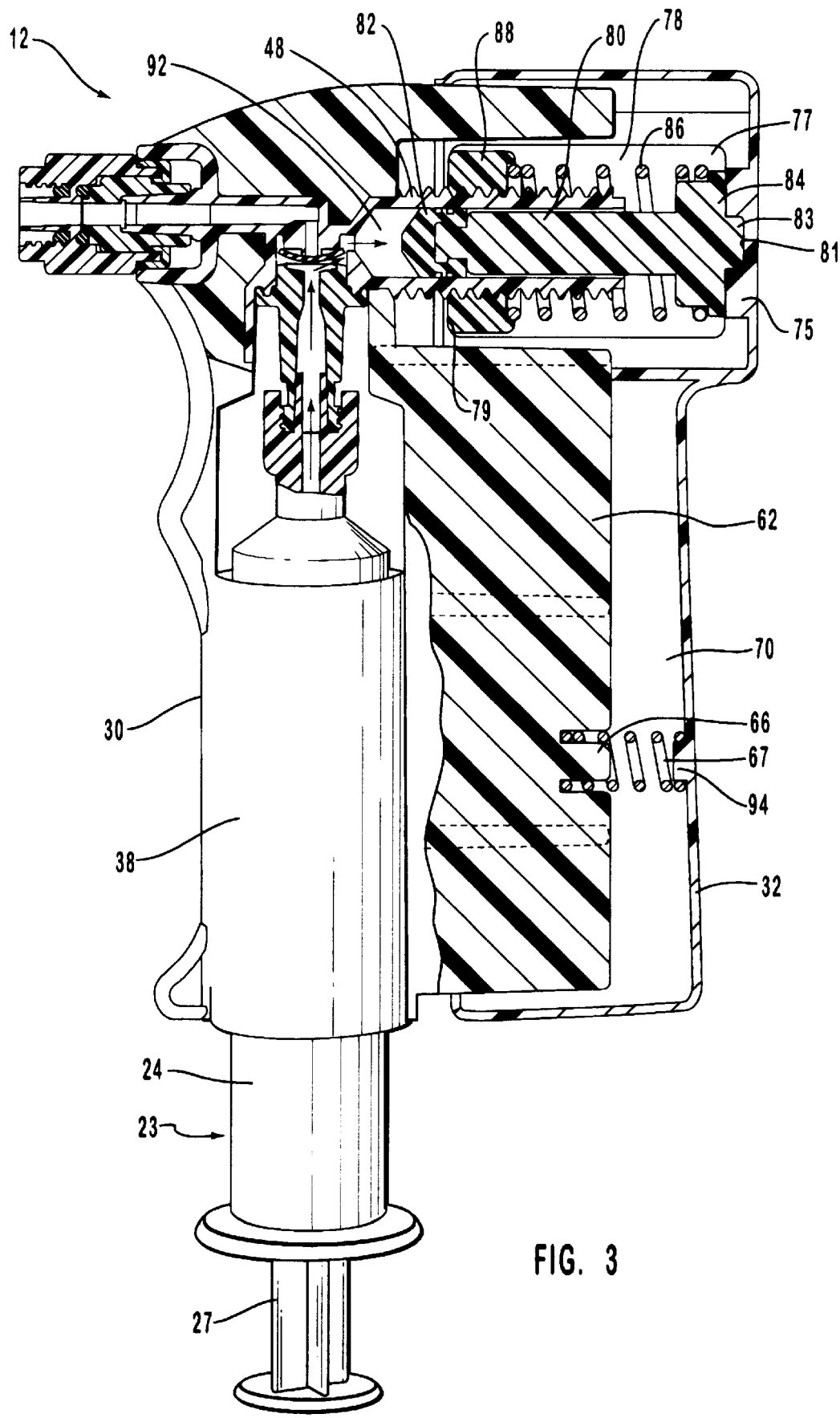
FIG. 3 is a partial cross-sectional side view of the pump shown in FIG. 2 in a first position.

The present invention also includes container means for holding a defined amount of fluid. By way of example and not by limitation, a syringe 23 is depicted having a barrel 24 with an open dispensing end 26. Positioned at dispensing end 26 is rotator connector 25, depicted here as a standard luer fitting. Slidably received within the opposing end of syringe 24 is a plunger 27. Finger rest 38 is used in part as a protective cover for the container means attached to pump 12. For example, once barrel 24 is fill with a desired fluid for dispensing, dispensing end 26 is slidably received within loading chamber 58 of finger rest 38 and advanced to stem 52. As a result of access opening 42, connector 25 of syringe 23 can be manually threaded onto threaded end 54 of stem 52, thereby forming a fluid connection therebetween. In this position, as depicted in FIG. 3, finger rest 38 substantially encloses syringe 23, thereby preventing syringe 23 from accidentally being bumped. Furthermore, even if syringe 23 was bumped, barrel 24 would bias against interior surface 57 of finger rest 38, thereby preventing syringe 23 from breaking off at stem 52.

Figure 2:
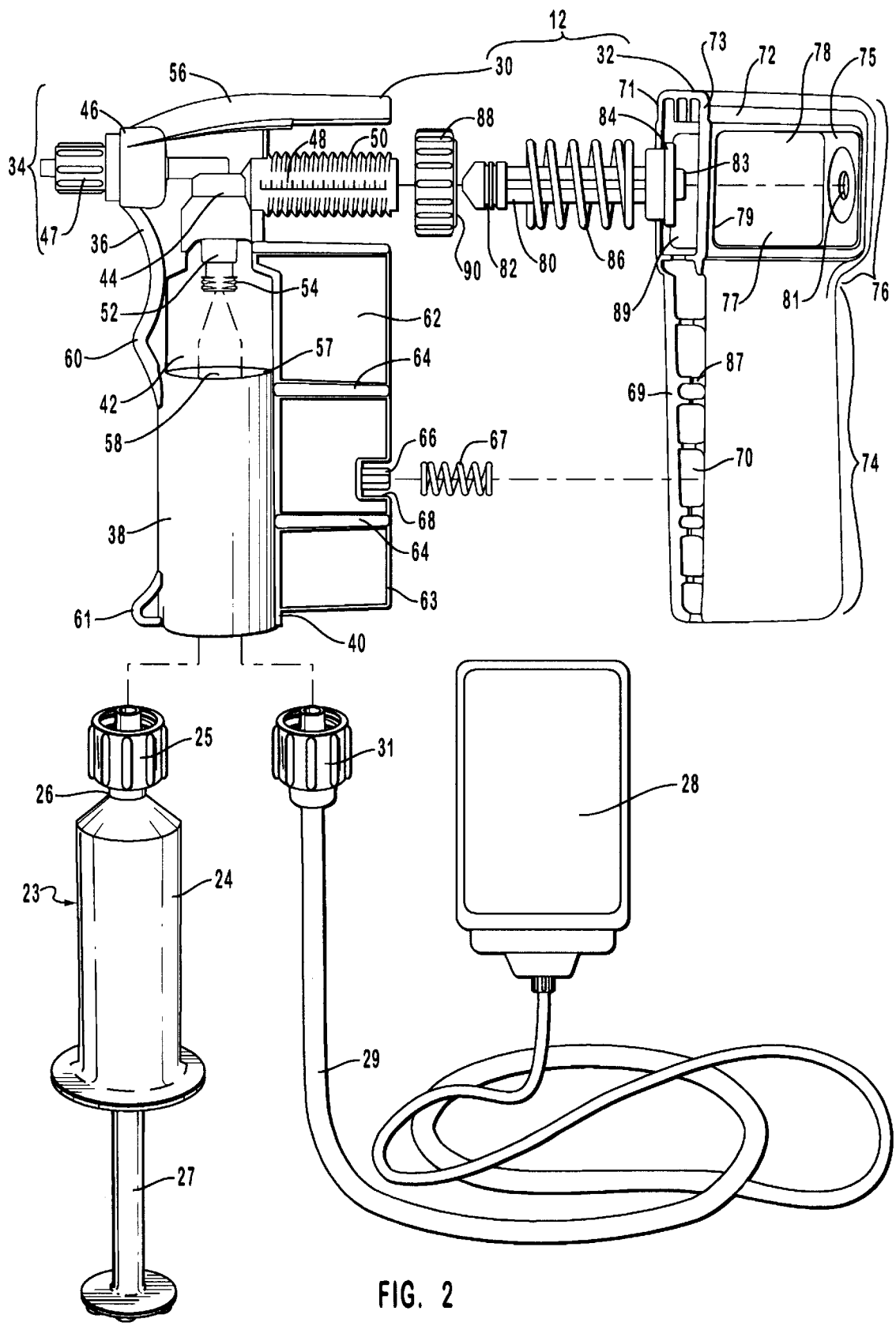
FIG. 2 is a partial side view of the pump shown in FIG. 1 in a disassembled condition with the handle thereof disposed in a perspective view.

Also depicted in FIG. 2, the container means can also include a flexible tube 29 having a fluid bag 28 attached at one end and a rotator connector 31 attached at the opposing end. Fluid bag 28 is fluid coupled to pump 12 by passing connector 31 through finger rest 38 and manually screwing to threaded end 54 of stem 52.

As depicted in FIG. 2, handle 32 has an elongated box shaped configuration that includes an elongated palm rest 74 with an enlarged plunger housing 76 mounted on the top thereof. Palm rest 74 has a front face 69 with a slot 70 extending inward and along the length thereof. Projecting into slot 70 are a plurality of guides 87. Guides 87 configure slot 70 so as to substantially complementary receive coupling plate 62 with alignment ridges 64 projecting therefrom.

Plunger housing 76 includes opposing sidewalls 71 and 72 which extend between a front face 73 and a back wall 75. Plunger housing 76 bounds a plunger chamber 77. A port 89 extends from front face 73 into plunger chamber 77. An annular recess 81 communicates with plunger chamber 77 and extends into back wall 75. A side opening 78 extends through each sidewall 71 and 72 of plunger housing 76 so as to each communicate with plunger chamber 77. Each side opening 78 is partially bounded by an inside edge 79 that is formed adjacent to and parallel with front face 73.

Pump 12 further includes a plunger 80 having an elastic tip 82 at one end and an enlarged annular flange 84 radially projecting out at the opposing end. A cylindrical post 83 projects from the opposing side of flange 84. A resiliently flexible spring 86 freely encircles plunger 80 and is configured to bias against flange 84. Finally, pump 12 also includes an annular control knob 88. Control knob 88 has a threaded aperture 90 extending therethrough. threaded aperture 90 is configured to rotatably engage threads 50 on the exterior of dispensing barrel 48.

As depicted in FIG. 3, pump 12 is assembled by initially positioning the spring 86 and the control knob 88 over tip 82 of plunger 80 and then inserting plunger 80 with spring 86 and control knob 88 into plunger chamber 77 through one of side openings 78. In this position, flange 84 is biased against back wall 75 with post 83 received within recess 81. Furthermore, control knob 88 is biased against the inside edge 79 of each side opening 78. Spring 86 is compressed between control knob 88 and flange 84, thereby holding plunger 80 within plunger chamber 77.

Next, tip 82 of plunger 80, projecting from plunger chamber 77, is slidably received within a barrel chamber 92 of dispensing barrel 48. Simultaneously, coupling plate 62 is slidably received within slot 70 of handle 74. Spring 67 mounted on post 66 of coupling plate 62 is also mounted on a spring post 94 positioned within palm rest 74. Control knob 88 is rotatably advanced on dispensing barrel 48, thereby securing handle 32 to body 30.

One of the unique benefits of pump 12 is that it can be operated using a single hand. During operation of pump 12, the user holds pump 12 by placing the palm of the hand against palm rest 74 and curling each of the fingers around finger grips 60 and 61 and finger rest 38. As the fingers are drawn towards the palm, springs 67 and 86 are compressed, thereby compressing body 30 against handle 32.

Figure 4:
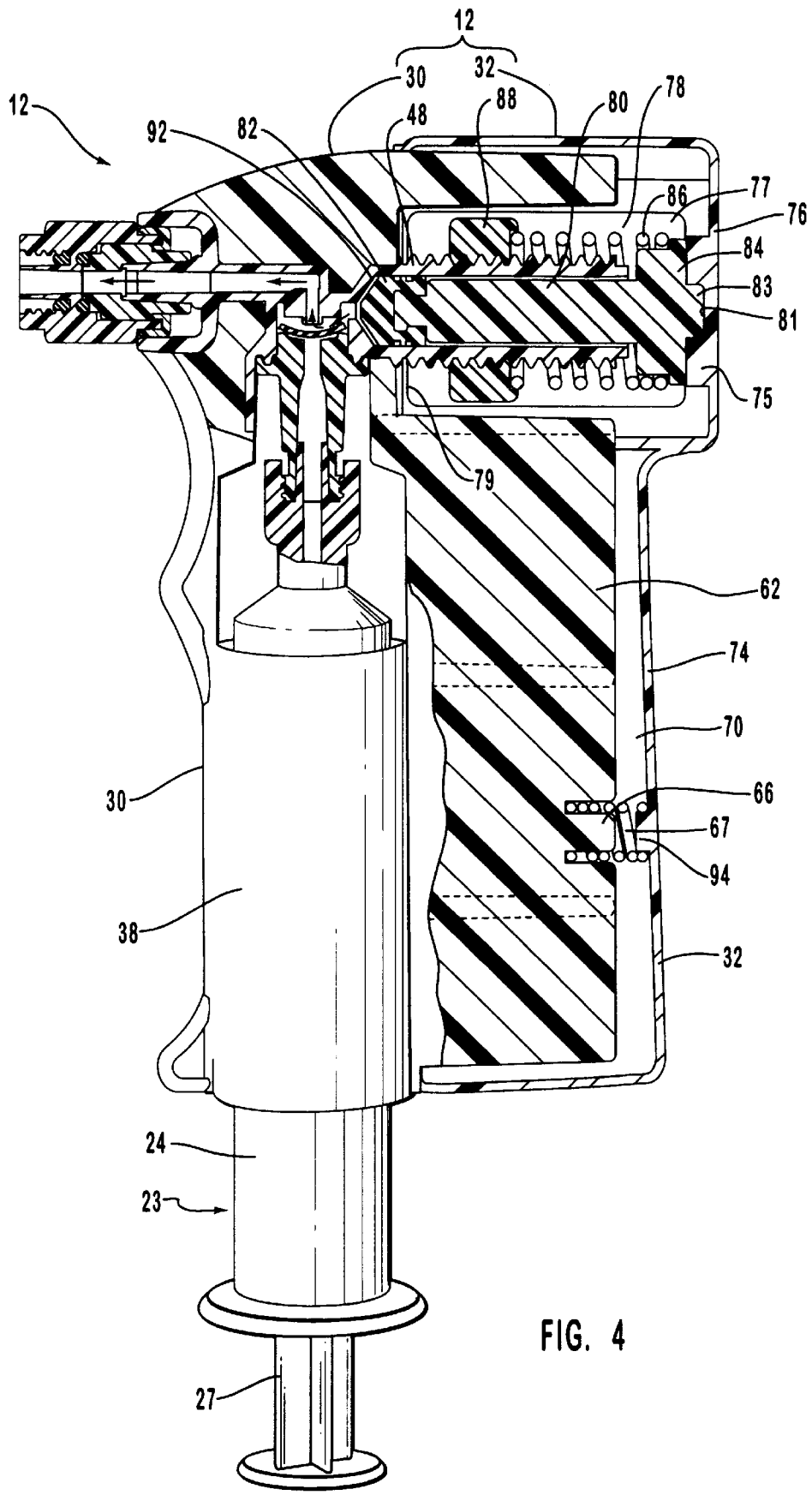
FIG. 4 is a partial cross-sectional view of the pump shown in FIG. 3 in a second position.

Plunger 12 operates between a first position and a second position. Depicted in FIG. 3, pump 12 is in the first position with body 30 and handle 32 biased apart by springs 67 and 86. In this first position, plunger 12 is retracted within barrel chamber 92. In the second position, as depicted in FIG. 4, body 30 and handle 32 are manually pressed together, thereby compressing springs 67 and 86 and advancing plunger 80 within barrel chamber 92.

The present invention also includes means for automatically retracting plunger 80 within dispensing barrel 48 after plunger 80 is manually advanced within dispensing barrel 48. By way of example and not by limitation, as the user extends the fingers curled around finger rest 38, springs 86 and 67 resiliently expand so as to automatically separate body 30 from handle 32, thereby also retracting plunger 80 within dispensing barrel 48 as discussed above. Accordingly, as an individual repeatedly squeezes and releases pump 12, plunger 80 repeatedly advances and retracts within dispensing barrel 48. There are of course a variety of alternative spring configurations that could work equally well to accomplish the retracting means. One such alternative is discussed with regard to the embodiment depicted in FIGS. 7–9. It is likewise envisioned that springs 86 and 67 could be replaced with alternative elastomeric materials such as rubber sleeves.

The present invention also includes regulating means partially mounted on the exterior surface of dispensing barrel 48 for selectively controlling how far plunger 80 can slide within dispensing barrel 48. By way of example and not by limitation, as control knob 88 is selectively advanced by rotation along the length of dispensing barrel 48, piston 80 moves to a corresponding position. For example, as control knob 88 is moved towards the free end of dispensing barrel 48, plunger 80 is correspondingly retracted within dispensing barrel 48. As a result, the volume of barrel chamber 92 unoccupied by plunger 80 is increased which, as will be discussed later, is filled with the fluid to be dispensed. Accordingly, as control knob 88 is advanced rearward, more fluid enters and is dispensed from barrel chamber 92. Conversely, as control knob 88 is advanced towards the front of dispensing barrel 48, less fluid enters and is subsequently dispensed from barrel chamber 92. Accordingly, by selectively positioning control knob 88 along dispensing barrel 48, a desired amount of fluid can be repeatedly dispensed from pump 12 at each squeezing thereof.

Figure 5:
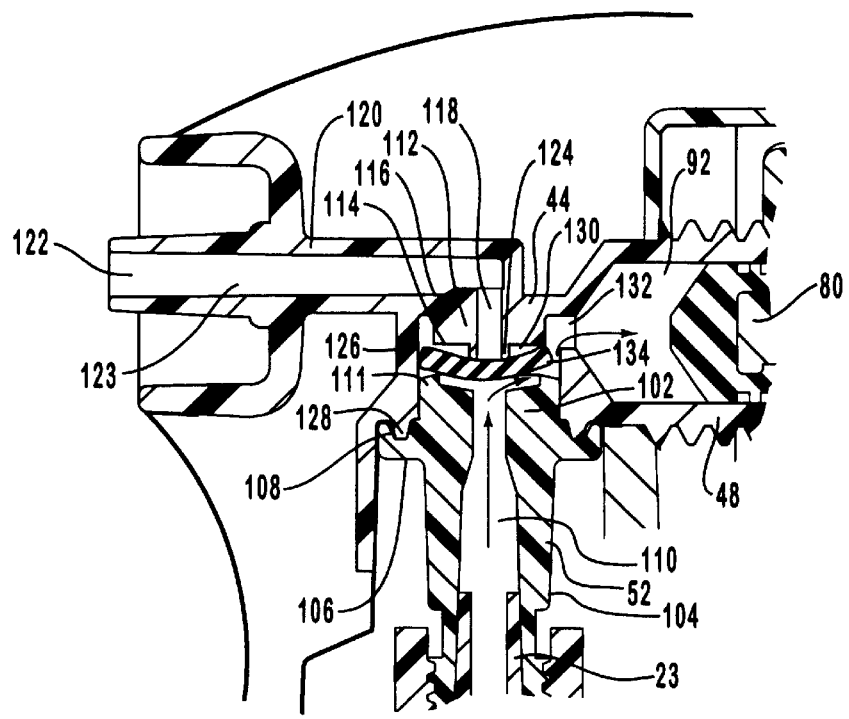
FIG. 5 is an enlarged cross-sectional side view of the valve housing of the pump shown in FIG. 3.

As depicted in FIG. 5, valve housing 44 includes a barrier wall 112 having a first side 114 and opposing second side 116 with a passageway 118 longitudinally extending therebetween. Formed on second side 116 of barrier wall 112 is a discharge tube 120 having an passageway 122 extending therethrough. Passageways 118 and 122 are in fluid communication and define an outlet passageway 123. Projecting from first side 114 of barrier wall 112 around the opening of passageway 118 is an annular sealing ring 124. An annular sidewall 126 projects down from first side 114 of barrier wall 112 around the perimeter thereof. Annular sidewall 126 terminates at an annular coupling ridge 128.

Stem 52 has an outer surface 104 extending between threaded end 54 and a top end 102. Also longitudinally extending between threaded end 54 and a top end 102 is an inlet passageway 110. Projecting from top end 102 of stem 52 around the outside edge thereof is an annular sealing lip 111. An annular flange 106 radially outwardly projects from outer surface 104. Recessed in one side of flange 106 is an annular groove 108 configured complementary to coupling ridge 128. During assembly, top end 102 of stem 52 is received within valve housing 44 such that coupling ridge 128 is received within groove 108. Coupling ridge 128 and groove 108 are secured together by an adhesive.

Extending between top end 102 of stem 52 and first side 114 of barrier wall 112 is a valve chamber 130. An opening 132 extends from valve chamber 130 to barrel chamber 92. Positioned within valve chamber 130 is a flexible, disc shaped gasket 134. In one embodiment, gasket 134 is formed from a silicone rubber. Under ambient conditions, gasket 134 is biased between sealing ring 124 and sealing ridge 111. During operation, as plunger 80 is retracted within dispensing barrel 48, a relative negative pressure is created within barrel chamber 92. As a result, fluid is sucked up from syringe 23, or some other attached fluid source, through inlet passageway 110 of stem 52 and into valve chamber 130 as depicted in FIG. 5. In turn, the outside perimeter of gasket 134 is flexed up and off of sealing lip 111 allowing the fluid to pass from valve chamber 130 and into barrel chamber 92 through opening 132. During the flow of fluid into barrel chamber 92, gasket 134 remains biased against sealing ring 12, thereby preventing fluid from passing into outlet passageway 123.

Figure 6:
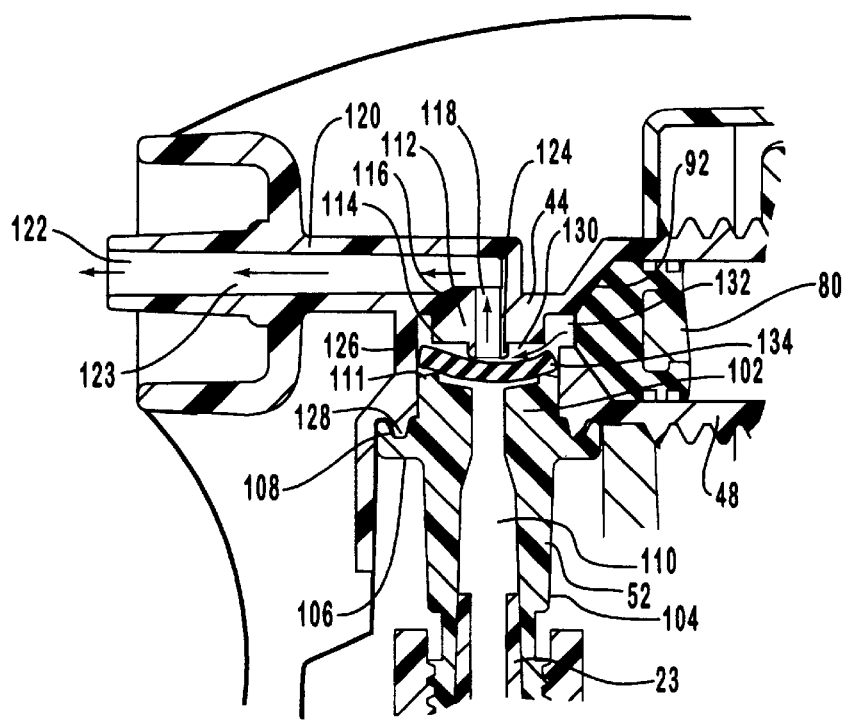
FIG. 6 is an enlarged cross-sectional side view of the valve housing of the pump shown in FIG. 4.

As depicted in FIG. 6, as plunger 80 is advanced within dispensing barrel 48, fluid within barrel chamber 92 is pushed through opening 132 into valve chamber 130. As a result of the direction of the fluid flow, gasket 134 bulges down and away from sealing ring 124 allowing fluid to into outlet passageway 123. During this fluid flow, gasket 134 remains pressed against sealing ridge 111, thereby preventing the fluid from passing into inlet passageway 110 of stem 52.

The present invention also includes valve means positioned within valve housing 44 for enabling fluid to pass from inlet passageway 110 to dispensing barrel 48 when plunger 80 is retracted within barrel 48 and for enabling fluid to pass from dispensing barrel 48 to outlet passageway 123 when plunger 80 is advanced within dispensing barrel 48. One example of the valve means includes gasket 134 interacting with valve chamber 130 as discussed above. Further disclosure with regard to the above valve assembly and alternatives thereto are found in U. S. patent application Ser. No. 09/198,608, entitled "Check Relief Valve", and filed Feb. 18, 1994 in the names of Mark A Christensen and Arlin D. Nelson (now abandoned), which is incorporated herein by specific reference.

In one embodiment of the present invention, the components of pump 12 may be injection molded from a plastic. In the preferred embodiment, body 30 and stem 52 are comprised of polycarbonate. In contrast, handle 32, control knob 88 and plunger 80 are comprised of ABS (Acrylonitrile Butadiene Styrene). By making the above elements out of different materials, the elements more easily slide together.

Figure 7:
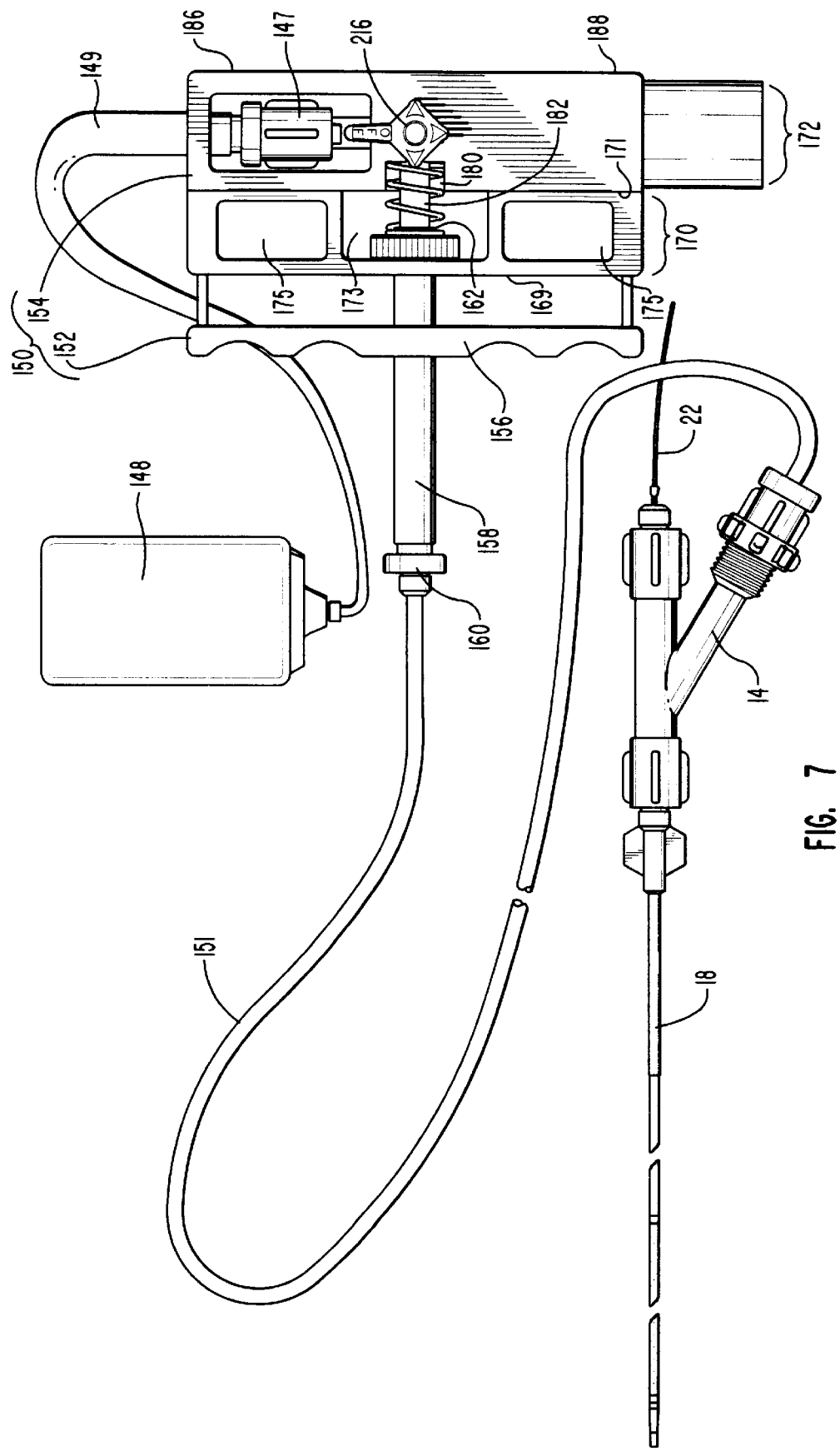
FIG. 7 is a side view of an alternative embodiment of a fluid infusion system.

Depicted in FIG. 7 is an alternative embodiment of a pump 150 for use in dispensing a fluid into infusion catheter 18 through three-way connector 14. Pump 150 is depicted as being fluid coupled to three-way connector 14 by way of a flexible tube 151. In alternative embodiments, pump 150 can be directly connected to three-way connector 14. As will be discussed later in greater detail, pump 150 can be fluid coupled to an external fluid source, such as fluid bag 148, by way of a flexible tube 149 having a rotator connector 147 mounted on the end thereof.

Pump 150 comprises a body 152 that is slidably mounted against a handle 154. Body 152 includes an elongated finger rest 156 with an elongated barrel 158 extending therethrough. Barrel 158 has a distal end 159 with a rotator connector 160 attached thereto and an opposing threaded proximal end 162. Body 154 includes a relatively thin, substantially rectangular front support 170 having a front edge 169 and a rear edge 171. A plunger chamber 173 transversely extends through front support 170. Side apertures 175 transversely extend through front support 170 on each side of plunger chamber 173.

Figure 8:
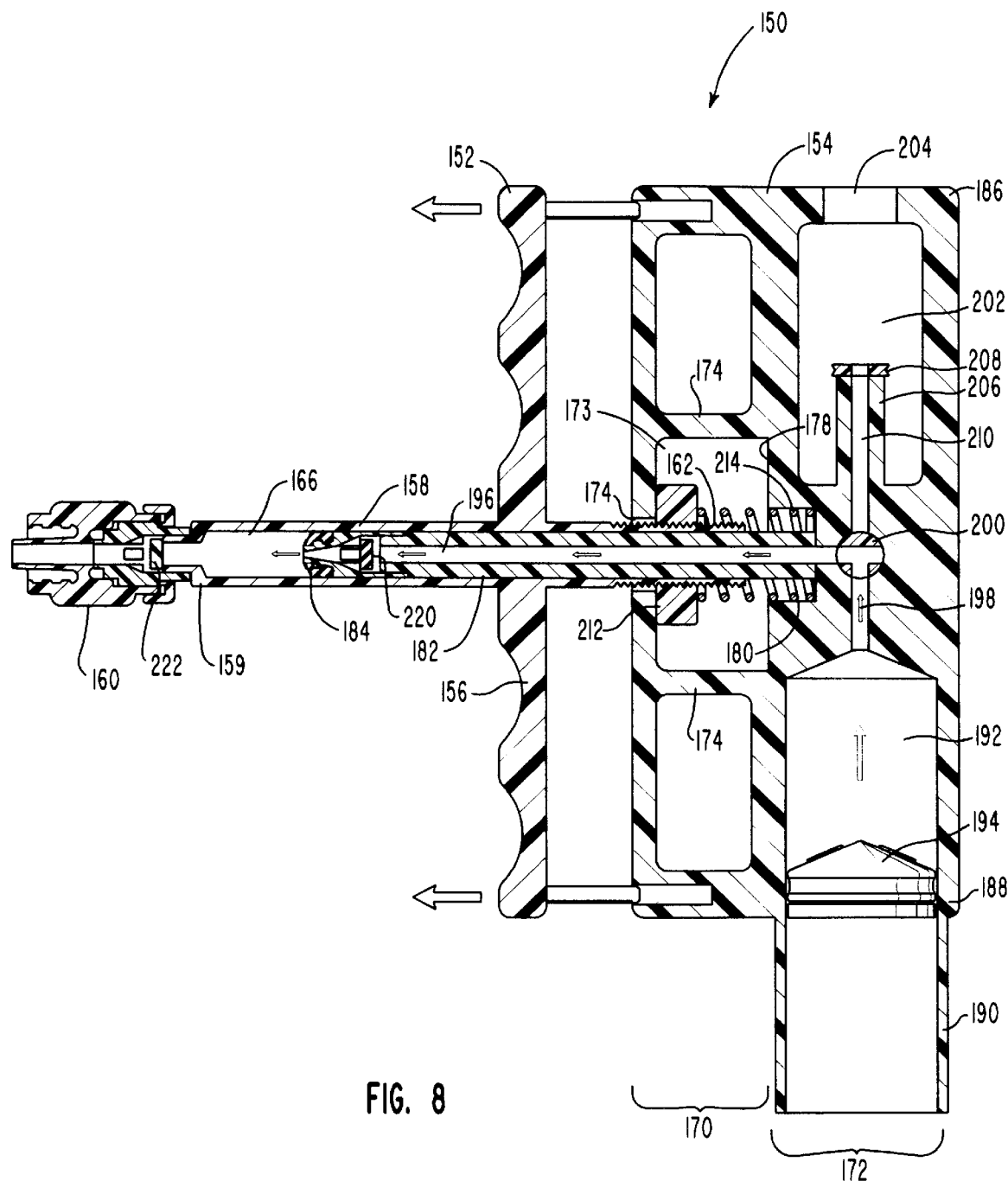
FIG. 8 is a cross-sectional side view of the pump shown in FIG. 7 in a first position.

Body 154 further includes a substantially cylindrical palm rest 172 mounted to rear edge 171 of front support 170. A spring recess 180 extends into palm rest 172 in alignment with front support 170. Projecting from spring recess 180 is an annular plunger 182. As depicted in FIG. 8, plunger 182 terminates at a sealing tip 184 and is slidably received within a barrel chamber 166 of barrel 158. Longitudinally extending from tip 184 of plunger 182 to ajunction 200 within palm rest 172 is a plunger passageway 196. A rotatable cock valve 216 is positioned at junction 200.

Palm rest 172 extends between a top end 186 and an opposing base end 188. Projecting from base end 188 is an annular extension sleeve 190. A cylindrical fluid reservoir extends through sleeve 190 and into base end 188 of palm rest 172. Slidably positioned with fluid reservoir 192 is a seal 194. A first passageway 198 extends from fluid reservoir 192 to junction 200, thereby enabling select fluid coupling between first passageway 198 and plunger passageway 196.

Transversely extending through palm rest 172 at top end 186 is an access opening 202. Extending through top end 186 into access opening 202 is an aperture 204. Projecting into access opening 202 opposite aperture 204 is a stem 206. Stem 206 terminates at a threaded end 208. A second passageway 210 longitudinally extends through stem 206 to junction 200, thereby enabling select fluid coupling between second passageway 210 and plunger passageway 196.

During assembly, proximal end 162 of barrel 158 is slidably received within a port 174 extending from front edge 169 of front support 170 to plunger chamber 173. A threaded control knob 212 is threadedly engaged on proximal end 162 of barrel 158. Control knob 212 has an outside diameter smaller than the inside diameter of port 174, thereby preventing separation of body 152 from handle 154. A resiliently compressible spring 214 has a first end disposed within spring recess 180 and an opposing second end continually biased against control knob 212. Under ambient conditions, spring 214 continually urges control knob 212 against front support 170.

Figure 9:
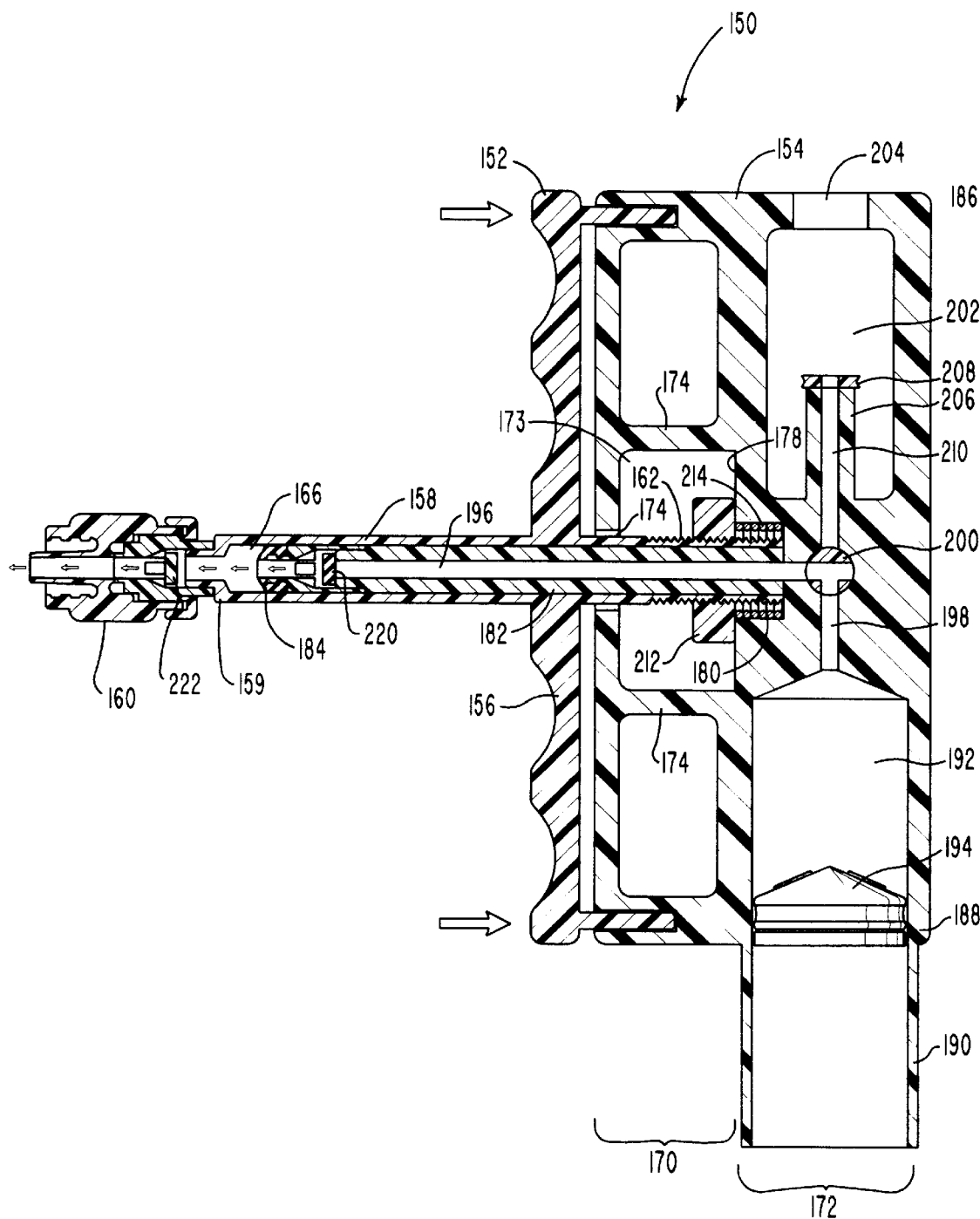
FIG. 9 is a cross-sectional side view of the pump shown in FIG. 8 in a second position.

During use, the user places the palm of the hand against palm rest 172 with the finger wrapped around finger rest 156. Pump 150 operates between a first position and a second position. Depicted in FIG. 8, pump 150 is in the first position. As shown therein, spring 214 biases body 152 and handle 154 apart, thereby retracting plunger 182 within barrel 158. As the fingers wrapped around finger rest 156 are drawn back towards to the users palm, spring 214 is compressed as body 152 and handle 154 are drawn together, thereby moving pump 150 into the second position as depicted in FIG. 9. As body 152 and handle 154 are drawn together, plunger 182 is advanced within barrel chamber 166.

As the users fingers are released, spring 214 automatically separates body 152 and handle 154, thereby forcing the retraction of plunger 182 within barrel chamber 166. Accordingly, plunger 182 can be repeatedly advanced and retracted within barrel chamber 166 by the user repeatedly squeezing and releasing pump 150. Control knob 212 selectively controls how far plunger 182 can advance within barrel chamber 166. Accordingly, by selectively positioning control knob 212, a desired amount of fluid is repeatedly aspirated and dispensed from pump 150.

Figure 10A:
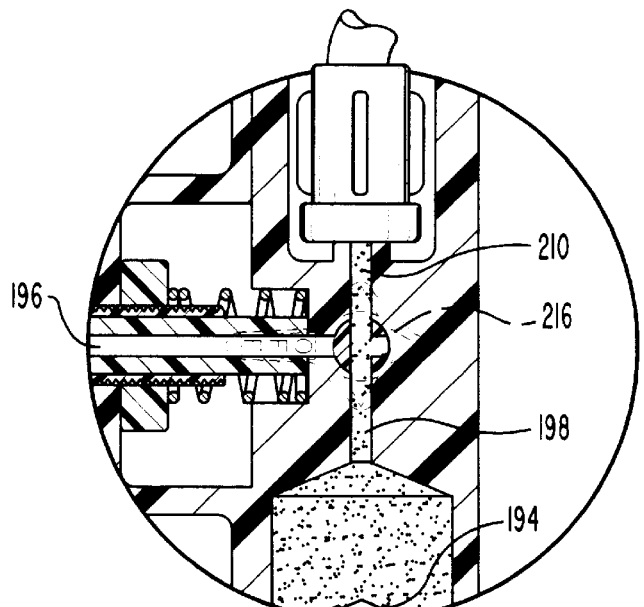
FIGS. 10A–10C are cross-sectional side views of the pump handle shown in FIG. 6 with the cock valve thereon moved to three separate positions.
Figure 10B:
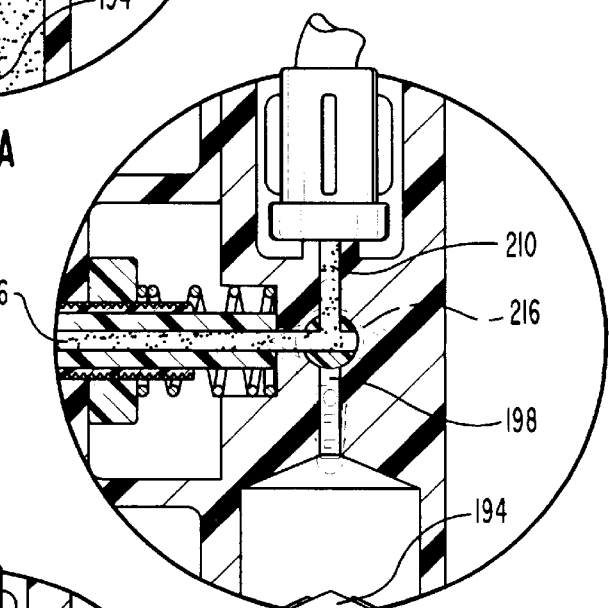
Figure 10C:
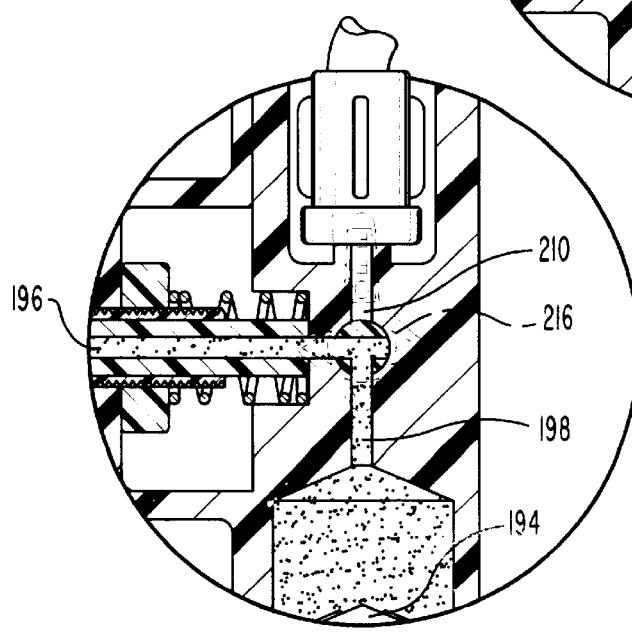

As depicted in FIGS. 10A–10C, check valve 216 can be selectively positioned to facilitate desired communications between first passageway 198, second passageway 210, and plunger passageway 196. For example, depicted in FIG. I OA check valve 216 is positioned to facilitate isolated fluid communication between first passageway 198 and second passageway 210. In this position, a fluid source can be secured to threaded end 208 of stem 206 so as to selectively fill fluid reservoir 192. As fluid reservoir 192 is filled, seal 194 automatically slides towards the end of sleeve 190.

Depicted in FIGS. 10B, check valve 216 is rotated to facilitate isolated fluid communication between second fluid passageway 210 and plunger passageway 196. In this configuration, fluid can be dispensed by pump 150 through a fluid source attached to stem 206. Alternatively, as depicted in FIG. I OC, check valve 216 is positioned to effect isolated fluid communication between first passageway 198 and plunger passageway 196. In this configuration, pump 150 dispenses fluid from fluid reservoir 192. As fluid is drawn from fluid reservoir 192, seal 194 automatically slides towards first passageway 198.

Fluid is advanced through pump 150 as a result of the interaction between two check valves. As depicted in FIG. 8, a first check valve 220 is positioned in plunger passageway 196 at the tip of plunger 182. A second check valve 222 is positioned between the tip of barrel 158 and rotator connector 160. Depicted in FIGS. 11A and 11B is an enlarged cross-sectional view of second check valve 222. Second check valve 222 is shown as comprising a cylindrical sleeve 224 projecting from distal end 159 of barrel 182. A valve passageway 226 extends through sleeve 224 and communicates with barrel chamber 196. Rotator connector 160 is secured by an adhesive to the exterior of sleeve 224. Rotator connector 160 has an interior surface 228 bounding a passageway 230 extending therethrough. Radially inwardly projecting from interior surface 228 of rotator connector 160 at a distance from sleeve 224 are a plurality of spaced apart retention shelves 232. Channels 234 extend between each retention shelf 232. Positioned between shelves 232 and sleeve 224 is an enlarged valve chamber 236. Freely housed within valve chamber 236 is a disk shaped gasket 238.

First check valve 220 has substantially the same structural elements as second check valve 222. Accordingly, like structural elements between first check valve 220 and second check valve 222 are identified by like reference characters.

During operation, as plunger 182 is advanced within barrel 158, as previously discussed, fluid within barrel chamber 166 pushes gasket 238 of first check valve 220 against shelves 224 as depicted in FIG. 8, thereby closing fluid communication between barrel chamber 166 and plunger passageway 196. Simultaneously, the fluid pushes gasket 238 of second check valve 222 against retention shelves 232, thereby allowing the fluid within barrel chamber 166 to pass around gasket 238, through channels 234, and out pump 150.

As plunger 182 is retracted within barrel 158 a relative negative pressure is produced within barrel chamber 196. As a result, gasket 238 of second check valve 222 seals against sleeve 224, as depicted in FIG. 9 and I lA. Simultaneously, gasket 238 of first check valve 220 is biased against retention shelves 232. The relative negative pressure created within barrel chamber 166 causes fluid to be drawn from either first passageway 198 or second passageway 210, depending on the position of stop cock 220, such that fluid passes down plunger passageway 196 and into barrel chamber 166. Once plunger 182 is fully retracted, plunger 182 can again be selectively advanced to dispel the fluid within barrel chamber 196. Accordingly, by repeatedly squeezing pump 150, fluid is repeatedly dispersed in desired predetermined amounts.

Figure 12:
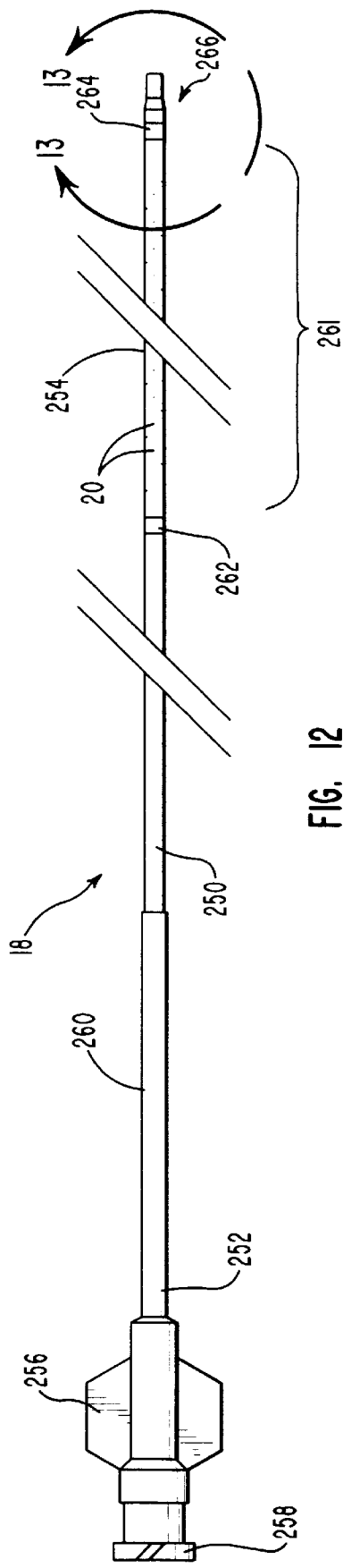
FIG. 12 is a side view of the infusion catheter shown in FIG. 1.
Figure 13:
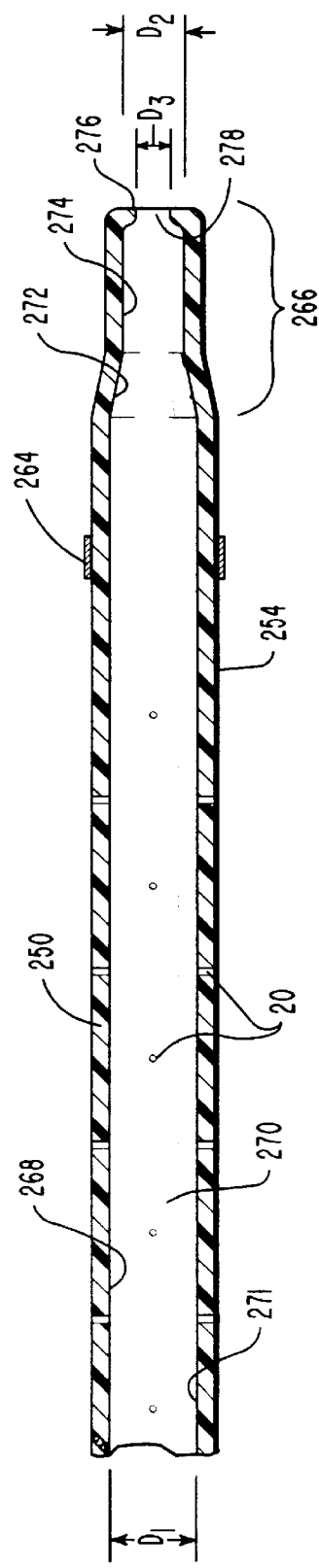
FIG. 13 is a cross-sectional side view of the distal end of the catheter shown in FIG. 12.

Depicted in FIG. 12, infusion catheter 18 has a body wall 250 longitudinally extending between a proximal end 252 and an opposing distal end 254. In one embodiment, infusion catheter 18 is formed from a nylon having a durometer of about shore 70D. Attached at proximal end 252 is a winged connector 256 having a threaded end 258. An outer sleeve 260 covers proximal end 252 of catheter 18 to help prevent kinking of body wall 250. Distal end 254 of catheter 18 includes a infusion length 261. Infusion length 261 has a plurality of infusion holes 20 extending therethrough, preferably in a double spiral configuration.

Individual infusion holes 20 are preferably spaced along infusion length 261 at regular intervals; for example, at intervals of about 0.050 inch. Infusion holes 20 are grouped together in sets of four holes radially spaced apart at 90° intervals. Each succeeding set of four holes is preferably rotated relative to the immediately proceeding set of four holes by about 18° in order to create a staggered hole arrangement that results in a more diverse spray pattern.

Thus, in a preferred embodiment, the second infusion hole will be radially spaced at an interval of 90° relative to the first infusion hole, the third infusion hole will be radially spaced 180° with respect to the first infusion hole, while the fourth infusion hole will be radially spaced 270° with respect to the first infusion hole. However, rather than being spaced at 360° (or 0°) relative to the first hole, the fifth infusion hole will begin a new group of four holes and be radially spaced from the first infusion hole by some amount between 1° and 89°, most preferably about 18°, since this value divides evenly into the 360° (and 90°) so that a very regular yet well spaced arrangement of holes can be attained.

Thereafter, the sixth, seventh and eighth holes will be radially spaced at 90° intervals relative to each other as in the first set of four holes. The ninth hole will begin the third set of four holes and will be offset from the fifth hole by, e.g., about 18° and the first hole by about 36°. This pattern repeats itself substantially regularly along the entire infusion length of the catheter. Other angles that divide evenly into 360°, but not necessarily 90° or 180° may also be used depending on the desired spray pattern. In addition, angles that do not divide evenly into 360° may be used in order to yield an even more randomized spray pattern.

Infusion length 261 can vary between about 5 cm to about 30 cm, with diminishing hole size as the number of holes is increased. The size of each infusion hole 20 will generally range between about 0.002"–0.006". Nevertheless, the size of catheter 18 and each infusion hole 20 can be altered, as can be the longitudinal spacing between holes 20, depending on the intended use of catheter 18.

The double spiral configuration of the present invention provides a significantly improved radial dispersion of thrombolytic fluid around the circumference of catheter 18, which helps to both chemically and mechanically break up the thrombus. The result is a more quickly and completely lysed blood clot using a reduced amount of thrombolytic fluid, which greatly contributes to the recovery and well-being of the patient. Further disclosure with regard to the size and patterning of infusion holes 20 is found in U.S. application Ser. No. 08/949,893 entitled “Catheter with Improved Spray Pattern for Pharmacal-Mechanical Thrombosis Therapy”, and filed Oct. 14, 1997 pending in the names of Jim D. Mottola, Stephen W. Carlstrom, and Andy E. Poursaid, which is incorporated herein by specific reference.

Encirclin body wall 250 at opposing ends of infusion length 261 is a first radiopaque band 262 and a second radiopaque band 264. Catheter 18 terminates at a tapered tip 266. As depicted in FIG. 13, body wall 250 has an interior surface 268 that bounds a lumen 270 longitudinally extending between proximal end 250 and distal end 254. Lumen 270 exits catheter 18 at tip 266 through a tip opening 278. Infusion holes 20 extend through body wall 250 to communicate with lumen 270. Interior surface 268 includes a cylindrical first portion having a diameter $D_1$ extending from proximal end 252 and a cylindrical second portion 274 having a diameter $D_2$ positioned at tip 266, Diameter $D_1$ being larger than diameter $D_2$. Interior surface 268 also includes an annular, sloped taper portion 272 extending between first portion 271 and second portion 274. Radially inwardly projecting from interior surface 268 at tip opening 278 is an annular sensing ridge 276. Sensing ridge 276 has an inside diameter $D_3$.

Depicted in FIG. 14, occluding wire 22 has a proximal end 282 and an opposing distal end 284. Positioned at proximal end 282 is an elongated positioning wire 286. Positioning wire 286 includes a cylindrical portion 287 having a diameter $D_4$ and a sloped tapered portion 288 projecting from the end thereof. Mounted on the end of tapered portion 288 is an enlarged substantially cylindrical occluding ball 290. Projecting from occluding ball 290 on the side opposite of tapered portion 288 is a flexible, coiled spring wire 292. Spring wire 292 has a maximum outer diameter $D_5$ and terminates at a smooth cap 294. As a result of spring wire 292 being formed in a coil, the wire forms a continuously encircling ridge 295 having a continuously encircling groove 296 formed between each of the coils.

By way of example and not by limitation, listed below is one typically set of dimensions for the above discussed diameters. The measurements given below are in inches:

D1=0.048±0.0015

D2=0.036±0.0005

D3=0.033±0.0005

D4=0.015±0.0005

D5=0.035±0.0015

Infusion catheter 18 can be directly inserted into the vascular system or placed using an introducer sheath. Typically, however, catheter 18 is positioned by first inserting a guidewire into the vascular system of the body of a patient. With the guidewire appropriately positioned, infusion catheter 18 is slid over the guidewire and fed to the distal end of the guidewire. The guidewire is then removed such that infusion catheter remains in the vascular system. Proximal end 252 of infusion catheter 18 is next coupled with three-way connector 14 and a select pump. Prior to pumping the fluid into infusion catheter 18, however, tip opening 278 must first be occluded. This is accomplished by advancing distal end 284 of occluding wire 22 into lumen 270 of catheter 18. As depicted in FIG. 15, occluding wire 18 is advanced until occluding ball 290 is seated and sealed against tapered portion 272. In this position, fluid can be pumped into lumen 270 for dispensing out through infusion holes 20.

In one embodiment of the present sensing means are provided for tactually sensing when distal end 284 of occluding wire 22 is adjacent to tip opening 278 of catheter 18. By way of example and not by limitation, diameter $D_3$ of sensing ridge 276 is smaller than diameter $D_5$ of spring wire 292. Accordingly, as spring wire 292 passes through sensing ridge 276, sensing ridge 276 vibrates over the discrete coils of spring wire 292. A surgeon is able to tactilely feel these vibrations through both occluding wire 22 and catheter 18. By sensing these vibrations, the surgeon is able to determine that occluding ball 290 is approaching seat 272. This warns the surgeon to carefully advance occluding wire 22 so that occluding ball 290 is not pushed through tip opening 278.

The present invention also includes means formed on the interior surface of the infusion catheter 18 for rubbing against spring wire 292 so as to transmit vibrations along occluding wire 22 when occluding wire 22 is advanced within the lumen of infusion catheter 18. By way of example and not by limitation, the means for rubbing against spring wire 292 comprises annular sensing ridge 276. In alternative embodiment, sensing ridge need not be annular but could comprise one or more fingers inwardly projecting from the interior surface 268 of catheter 18. Furthermore, sensing ridge 276 need not be positioned at tip opening 278 but could be positioned at alternative locations along the length of catheter 18.

Means mounted on occluding wire 22 are also provided for rubbing against the sensing ridge 276 so as to transmit vibrations along the occluding wire 22 when occluding wire 22 is advanced within the lumen of infusion catheter 18. By way of example, the means for rubbing against sensing ridge 276 comprises spring wire 292 as described above. In alternative embodiments, a non-coiled wire having ridges projecting therefrom would also work.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A hand pump for dispensing a fluid, the hand pump comprising:
   (a) a dispensing barrel having a chamber;
   (b) a finger rest rigidly attached to the dispensing barrel, the finger rest having a loading chamber formed therein, the loading chamber being fluid coupled to the chamber of the dispensing barrel through an inlet passageway;
   (c) a plunger having a tip end slidably received within the chamber of the dispensing barrel; and
   (d) a handle mounted to the plunger.

2. A hand pump as recited in claim 1, further comprising a dual check valve to allow control of direction of fluid flow.

3. A hand pump as recited in claim 1, further comprising graduations on the outside surface of the dispensing barrel to allow for accurate measurement of the required dose.

4. A hand pump as recited in claim 1, further comprising means for automatically retracting the plunger within the dispensing barrel after the plunger is manually advanced within the dispensing barrel.

5. A hand pump as recited in claim 4, wherein the means for automatically retracting the plunger comprises a spring disposed between the handle and the finger rest.

6. A hand pump as recited in claim 1, further comprising:
   (a) a fluid supply syringe configured to be received within the loading chamber such that the supply syringe is substantially enclosed therein; and
   (b) means for fluid coupling the supply syringe to the inlet passageway.

7. A hand pump as recited in claim 1, further including:
   (a) a fluid supply tubing and reservoir configured to be received within the loading chamber; and
   (b) means for fluid coupling of the supply tubing and reservoir to the inlet passageway.

8. A hand pump as recited in claim 1, further comprising:
   (a) a valve housing directly fluid coupled to an outlet passageway, the inlet passageway, and the chamber of the dispensing barrel; and
   (b) valve means positioned within the valve housing for enabling fluid to pass from the inlet passageway to the dispensing barrel when the plunger is retracted within the barrel and for enabling fluid to pass from the dispensing barrel to the outlet passageway when the plunger is advanced within the dispensing barrel.

9. A hand pump for dispensing a fluid, the hand pump comprising:
   (a) a body including:
      (i) a dispensing barrel having a chamber extending between a first end and an opposing free second end; and
      (ii) a finger rest attached to the first end of the barrel;
   (b) a plunger having a tip end slidably received within the second end of the dispensing barrel;
   (c) a handle mounted to the plunger;
   (d) container means for holding a defined amount of fluid, the container means being removably attached to the body; and
   (e) means for fluid coupling the container means to the dispensing barrel when the container means is attached to the body.

10. A hand pump as recited in claim 9, wherein the means for fluid coupling the container means to the dispensing barrel comprises the body, wherein the body further includes:
   (a) a valve housing directly fluid coupled to an outlet passageway, an inlet passageway, and the chamber of the dispensing barrel at the first end thereof, the inlet passageway having a first end remote from the valve housing;
   (b) valve means positioned within the valve housing for enabling fluid to pass from the inlet passageway to the dispensing barrel when the plunger is retracted within the barrel and for enabling fluid to pass from the dispensing barrel to the outlet passageway when the plunger is advanced within the dispensing barrel; and
   (c) means for fluid coupling the container means to the first end of the inlet passageway.

11. A hand pump as recited in claim 10, further comprising a rotator connector mounted to the outlet passageway at the end thereof remote from the valve housing.

12. A hand pump as recited in claim 9, wherein the body further comprises a loading chamber recessed therein, the loading chamber being configured to receive at least a portion of the container means when the container means is attached to the body.

13. A hand pump as recited in claim 12, wherein the loading chamber is recessed within the finger rest.

14. A hand pump as recited in claim 9, wherein the container means comprises a syringe.

15. A hand pump as recited in claim 9, wherein the container means comprises a fluid bag having a flexible tube attached thereto.

16. A hand pump as recited in claim 9, further comprising a resiliently compressible spring disposed between the body and the handle.

17. A hand pump comprising:
   (a) a dispensing barrel having an exterior surface and a chamber each extending between a first end and an opposing free second end;
   (b) an elongated finger rest rigidly mounted to the dispensing barrel;
   (c) a plunger having a tip end and an opposing tail end, the tip end being slidably received within the second end of the barrel;
   (d) a handle mounted to the plunger; and
   (e) regulating means partially mounted on the exterior of the dispensing barrel for selectively controlling how far the plunger can slide within the dispensing barrel.

18. A hand pump as recited in claim 17, further comprising graduations marked on the outside surface of the dispensing barrel to allow for accurate measurement of the required dose.

19. A hand pump as recited in claim 17, wherein the regulating means comprises:
   (a) the handle having a plunger chamber communicating with the exterior through a port, the second end of the dispensing barrel being disposed within the plunger chamber through the port;
   (b) a knob threadedly mounted on the exterior of the dispensing barrel, the knob being captured within the plunger chamber.

20. A hand pump as recited in claim 19, further comprising a spring encircling the plunger and extending between the knob and the tail end of the plunger.

21. A hand pump as recited in claim 19, further comprising a side opening extending through the plunger chamber to facilitate select rotation of the knob.

22. A hand pump as recited in claim 19, wherein the handle further comprising an elongated palm rest projecting from the plunger chamber.

23. A hand pump as recited in claim 19, further comprising:
   (a) an alignment plate projecting from the finger rest; and
   (b) the handle further comprising an elongated palm rest projecting from the plunger chamber, the palm rest having an elongated slot formed therein, the alignment plate being slidably positioned within the slot.

24. A hand pump as recite in claim 17, further comprising:
   (a) the handle having a palm rest attached thereto; and
   (b) the plunger having a plunger passageway longitudinally extending therethrough and into the palm rest.

25. A hand pump as recited in claim 24, further comprising a fluid chamber formed within the palm rest and fluid coupled with the plunger passageway.

26. A hand pump as recited in claim 24, further comprising:
   (a) first check valve means positioned within the plunger passageway for enabling fluid to pass from the plunger passageway into the dispensing barrel when the plunger is retracted within the dispensing barrel; and
   (b) second check valve means positioned within the first end of the dispensing barrel for enabling fluid within the dispensing barrel to pass through the first end thereof when the plunger is advanced within the dispensing barrel.

27. A hand pump for dispensing a fluid, the hand pump comprising:
   (a) an integral body comprising:
      (i) a head including a valve housing fluid coupled to an inlet passageway, an outlet passageway, and a dispensing barrel,
      (ii) a finger rest projecting from the head;
   (b) a handle slidably attached to the body;
   (c) a plunger mounted to the handle and slidably received within the dispensing barrel; and
   (d) a spring disposed between the handle and the body.

28. A hand pump as recited in claim 27, further comprising valve means positioned within the valve housing for enabling fluid to pass from the inlet passageway to the dispensing barrel when the plunger is retracted within the barrel and for enabling fluid to pass from the dispensing barrel to the outlet passageway when the plunger is advanced within the dispensing barrel.

29. A hand pump as recited in claim 27, further comprising a loading chamber recessed within the finger rest, the loading chamber being in fluid communication with the inlet passageway.

30. A hand pump as recited in claim 27, further comprising a fluid supply syringe having a barrel for holding the fluid and being configured to be received with the loading chamber for fluid coupling with the inlet passageway.

31. A hand pump as recited in claim 27, further comprising:
   (a) the handle having a plunger chamber communicating with the exterior through a port, the second end of the dispensing barrel being disposed within the plunger chamber through the port; and
   (b) a knob threadedly mounted on the exterior of the dispensing barrel, the knob being captured within the plunger chamber.

32. A hand pump as recited in claim 31, further comprising a side opening extending through the plunger chamber to facilitate select rotation of the knob.

33. A hand pump as recited in claim 31, wherein the handle further comprises an elongated palm rest projecting from the plunger chamber.

34. A hand pump as recited in claim 27, further comprising:
   (a) an alignment plate projecting from the finger rest; and
   (b) the handle further comprising an elongated palm rest projecting from the plunger chamber, the palm rest having an elongated slot formed therein, the alignment plate being slidably positioned within the slot.

* * * * *

UNITED STATES PATENT AND TRADEMARK OFFICE
CERTIFICATE OF CORRECTION

Figure 14:
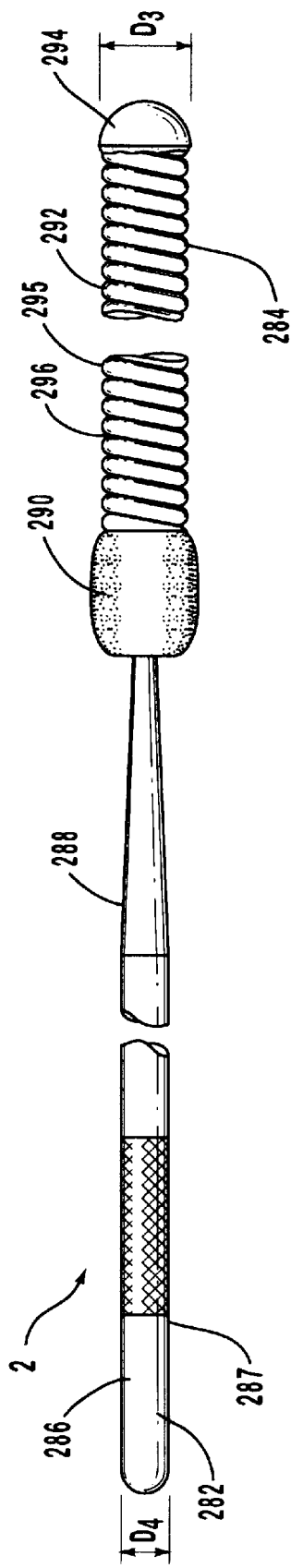
FIG. 14 is a side view of the occluding wire shown in FIG. 1.
Figure 15:
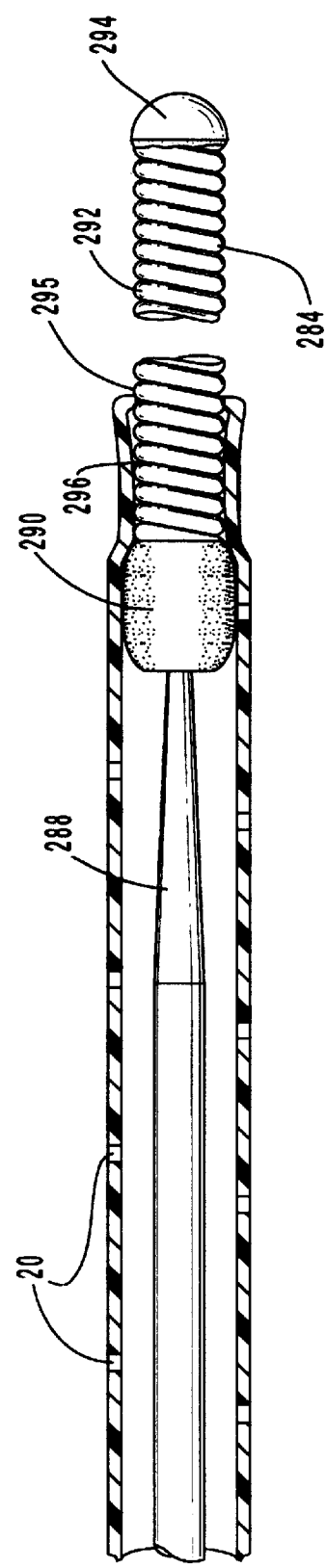
FIG. 15 is a partial cross-sectional side view of the occluding wire shown in FIG. 14 being inserted into the distal end o f the infuision catheter shown in FIG. 13.

PATENT NO. : 5,951,517
DATED : September 14, 1999
INVENTOR(S) : Fred P. Lampropoulos, Jerry L. Trujillo, M. Mary Sinnott It is certified that error appears in the above-identified patent and that said Letters Patent is hereby corrected as shown below:

Fig. 14, change the label "2" to --22--

Col. 2, line 5, after "side" change "opening" to --openings--

Col. 2, line 42, before "access" change "block" to --blocks--

Col. 6, line 11, after "hemostasis" change "valves" to --valve--

Col. 7, line 43, after "substantially" change "complementary" to --complementarily--
Col. 7, line 63, before "aperture" change "threaded" to --Threaded--

Col. 9, line 33, after "Under" change "ambient" to --resting--

Col. 9, line 45, before "thereby" change "12" to --124--

Col. 9, line 51, after "fluid to" insert --flow--

Col. 9, line 67, after "Mark" change "A" to --A.--

Col. 10, line 67, after "Under" change "ambient" to --resting--

Col. 11, lines 30-31, after "FIG." change "I OA" to --10A--

Col. 11, line 37, after "Depicted in" change "FIGS." to --FIG.--

Col. 11, line 42, after "FIG." change "I OC" to --10C--

UNITED STATES PATENT AND TRADEMARK OFFICE
CERTIFICATE OF CORRECTION

PATENT NO. : 5,951,517
DATED : September 14, 1999
INVENTOR(S) : Fred P. Lampropoulos, Jerry L. Trujillo, M. Mary Sinnott It is certified that error appears in the above-identified patent and that said Letters Patent is hereby corrected as shown below:

Col. 12, line 19, after "and" change "I 1A" to --11A--

Col. 12, line 24, after "stop cock" change "220" to --216--

Col. 12, line 36, after "shore" change "70D" to --70D--

Col.13, line 29, before "body" change "Encirclin" to --Encircling--

Col. 14, line 23, after "present" insert --invention--

Signed and Sealed this

Thirty-first Day of October, 2000

Attest:

Q. TODD DICKINSON

Attesting Officer

Director of Patents and Trademarks